(12) United States Patent
Knies et al.

(10) Patent No.: US 8,686,173 B2
(45) Date of Patent: Apr. 1, 2014

(54) PREPARATION OF 1,3,5-TRIETHY1-2,4,6-TRIHYDRIDO-2,4,6-TRIETHYLAMINO-1,3,5-TRIAZA-2,4,6-TRISILACYCLOHEXANE

(75) Inventors: Wolfgang Knies, Burghausen (DE); Hans Eiblmeier, Burghausen (DE)

(73) Assignee: Wacker Chemie AG, Munich (DE)

( * ) Notice: Subject to any disclaimer, the term of this patent is extended or adjusted under 35 U.S.C. 154(b) by 218 days.

(21) Appl. No.: 13/175,337

(22) Filed: Jul. 1, 2011

(65) Prior Publication Data
US 2012/0004435 A1   Jan. 5, 2012

(30) Foreign Application Priority Data

Jul. 2, 2010  (DE) .......................... 10 2010 030 895

(51) Int. Cl.
*C07F 7/02* (2006.01)
(52) U.S. Cl.
USPC ............ 556/412; 556/407; 556/409; 556/410

(58) Field of Classification Search
None
See application file for complete search history.

(56) References Cited

U.S. PATENT DOCUMENTS

| 4,594,330 A | 6/1986 | Nakano |
| 7,887,881 B2 | 2/2011 | Lu |
| 2006/0194707 A1* | 8/2006 | Lu ................................ 510/245 |

FOREIGN PATENT DOCUMENTS

CN        1780889 A      5/2006

OTHER PUBLICATIONS

Sergeeva et al., Obscej Chimii, 1962, 32, p. 1987-1993.

* cited by examiner

*Primary Examiner* — Sudhakar Katakam
(74) *Attorney, Agent, or Firm* — RatnerPrestia

(57) ABSTRACT

A process for preparing 1,3,5-triethyl-2,4,6-trihydrido-2,4,6-triethylamino-1,3,5-triaza-2,4,6-trisilacyclohexane, wherein trichlorosilane is reacted with ethylamine in a solvent.

4 Claims, No Drawings

PREPARATION OF 1,3,5-TRIETHY1-2,4,6-TRIHYDRIDO-2,4,6-TRIETHYLAMINO-1,3,5-TRIAZA-2,4,6-TRISILACYCLOHEXANE

CROSS REFERENCE TO RELATED APPLICATIONS

This application claims priority of German patent application number 10 2010 030 895.1, filed 2 Jul. 2010, the entirety of which application is incorporated herein by reference.

BACKGROUND OF THE INVENTION

In semiconductor manufacture, because of recent methods for production of SiO, SiN, SiON and SiOC layers, there is a search for reactive compounds which can either be deposited directly in the CVD (chemical vapor deposition) method or applied in the ALD (atomic layer deposition) method, and reacted in a subsequent reaction step.

One molecule group suitable for this purpose is aminosilanes or silazanes. In addition to the monomeric compounds, oligosilanes have also been studied.

The compound named in the title (referred to hereinafter as trisilazane for short) was mentioned as early as 1962 by Sergeeva et al. (ZH. Obschei Khimii 1962, 32, 1987 ff), and some of its properties were described, but a synthesis was not described.

SUMMARY OF THE INVENTION

The invention provides a process for preparing 1,3,5-triethyl-2,4,6-trihydrido-2,4,6-triethylamino-1,3,5-triaza-2,4,6-trisilacyclohexane, wherein trichlorosilane is reacted with ethylamine in a solvent.

DETAILED DESCRIPTION OF THE INVENTION

It has now been found that the reaction of trichlorosilane with ethylamine in a solvent forms tris(ethylamino)silane ($(EtNH)_3SiH$) expected at first only to a minor extent, and instead preferentially forms the trisilazane.

The solvent is preferably an aliphatic hydrocarbon with preferably $C_4$ to $C_{15}$, more preferably $C_5$ to $C_{10}$, especially preferably $C_6$ to $C_8$, preference being given to pentane, hexane, heptane, octane, isooctane, nonane, decane, particular preference to isohexane.

The process according to the invention is performed preferably at a temperature below 20° C., preferably below 5° C., more preferably below −10° C. to −50° C., and a pressure of 900 to 1100 hPa.

The ethylamine is preferably introduced into the gas space of the reactor and the metered addition is preferably selected such that the internal temperature of the reactor does not exceed −10° C.

Based on one mole of trichlorosilane, 6 to 10 mol of ethylamine, more preferably 6.2 to 7 mol of ethylamine, and 200 to 1500 g of solvent, more preferably 800 to 1000 g of solvent, are used.

At the end of the reaction, the suspension obtained is preferably filtered and preferably washed with solvent, and the solution obtained is preferably distilled, the distillation conditions being such that the temperature is preferably below 320° C., more preferably 100 to 150° C., and the pressure is preferably standard pressure at 900 to 1100 hPa down to reduced pressure, more preferably below 1 mbar.

In the context of the present invention, all parts and percentages stated, unless stated otherwise, are based on weight. Unless stated otherwise the working pressure is that of the surrounding atmosphere, i.e. about 900 to 1100 hPa, and unless stated otherwise the temperature is room temperature, i.e. about 20° C. or a temperature which is established on combination of the reactants at room temperature without additional heating or cooling. All viscosity data cited shall be based on a temperature of 25° C.

EXAMPLE

A jacketed vessel with stirrer, jacketed coil condenser, temperature sensor and dropwise addition line was initially charged with 1410 g of isohexane. To this were added 244 g of trichlorosilane. Subsequently, the solution was cooled to −40° C. and 550 g of ethylamine were introduced into the gas space of the reactor. The metered addition was selected such that the internal temperature of the reactor did not exceed −10° C. A white suspension formed, which was warmed gradually to 20° C. Subsequently, the suspension was filtered, the solids were washed with further isohexane and the solution obtained was distilled. At about 130° C. and pressure 0.1 mbar, a fraction was obtained which contained the trisilazane in a purity of more than 98% (determined by means of gas chromatography).

The invention claimed is:

1. A process for preparing 1,3,5-triethyl-2,4,6-trihydrido-2,4,6-triethylamino-1,3,5-triaza-2,4,6-trisilacyclohexane, which comprises reacting trichlorosilane with ethylamine in a solvent.

2. The process as claimed in claim 1, wherein the solvent is a $C_5$ to $C_{10}$ aliphatic hydrocarbon.

3. The process as claimed in claim 1, wherein the solvent is initially charged to a reactor and trichlorosilane is added, then the solution is cooled to −10 to −50° C. and ethylamine is introduced into the gas space of the reactor at a rate such that the internal temperature of the reactor does not exceed −10° C.

4. The process as claimed in claim 2, wherein the solvent is initially charged to a reactor and trichlorosilane is added, then the solution is cooled to −10 to −50° C. and ethylamine is introduced into the gas space of the reactor at a rate such that the internal temperature of the reactor does not exceed −10° C.

* * * * *